United States Patent [19]

Hiratsuka et al.

[11] Patent Number: 4,753,531
[45] Date of Patent: Jun. 28, 1988

[54] FLAT CONTAINER TYPE ANALYTICAL INSTRUMENT

[75] Inventors: Nobuo Hiratsuka; Asaji Kondo, both of Asaka, Japan

[73] Assignee: Fuji Photo Film Co., Ltd., Kanagawa, Japan

[21] Appl. No.: 873,284

[22] Filed: Jun. 4, 1986

Related U.S. Application Data

[63] Continuation of Ser. No. 676,054, Nov. 29, 1984, abandoned.

[30] Foreign Application Priority Data

Nov. 29, 1983 [JP] Japan .......................... 58-225187
Nov. 29, 1983 [JP] Japan .......................... 58-225188
Nov. 29, 1983 [JP] Japan .......................... 58-225189

[51] Int. Cl.$^4$ .................... G01N 21/01; G01N 1/10
[52] U.S. Cl. .................................. 356/246; 422/102
[58] Field of Search ............. 356/239, 244, 246, 432; 422/56, 58, 102

[56] References Cited

U.S. PATENT DOCUMENTS 3,690,836  9/1972  Buissiere et al. .................. 422/56
3,698,822 10/1972  Polanyi ............................ 356/246
4,515,889  5/1985  Klose et al. ...................... 422/102

FOREIGN PATENT DOCUMENTS 0201837 12/1982  Japan ............................. 356/246

Primary Examiner—Davis L. Willis
Assistant Examiner—S. A. Turner
Attorney, Agent, or Firm—Jules E. Goldberg

[57] ABSTRACT

An integral flat container type analytical instrument for use in the quantitative analysis of an analyte present in a liquid sample which has a reaction chamber and an observation chamber associated with each other so as to allow a liquid to flow therebetween characterized in that: at least part of the wall of said reaction chamber is made of a flexible material; said observation chamber is provided with wall parts which are made of a transparent material and opposed to each other in such a manner that their relative positions are fixed to provide a given light path; and no partition wall preventing the free flow of the liquid substantially exists between said reaction chamber and said observation chamber. A method for optical measurement of an analyte in a liquid sample utilizing said analytical instrument is also disclosed.

8 Claims, 3 Drawing Sheets

FIG. 1-A
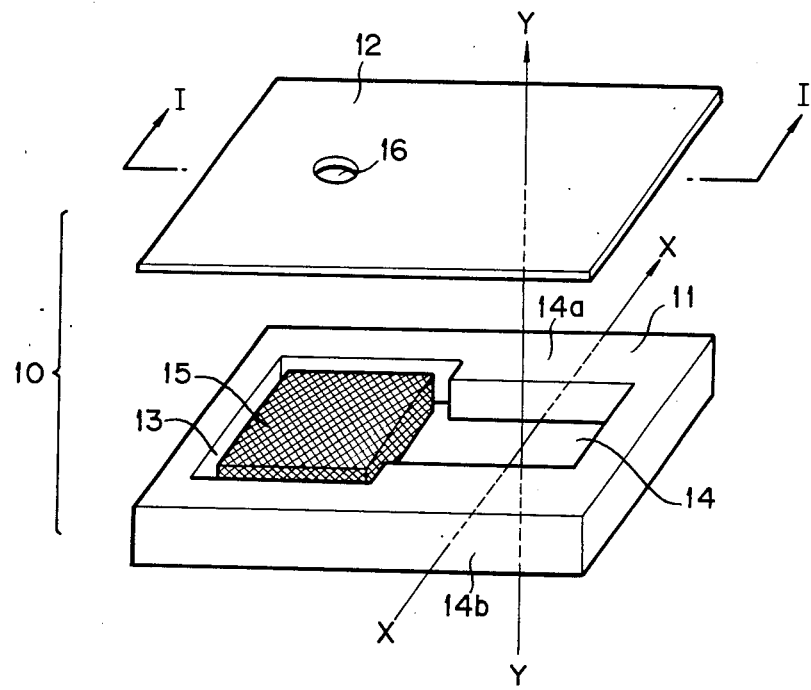
FIG. 1-B
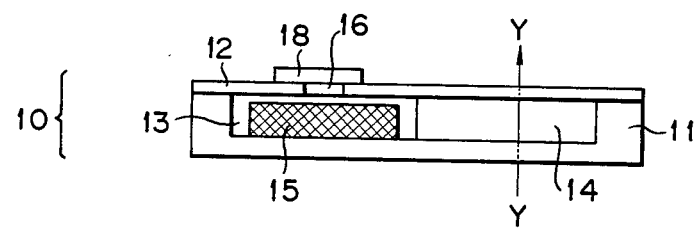

FIG. 2-A
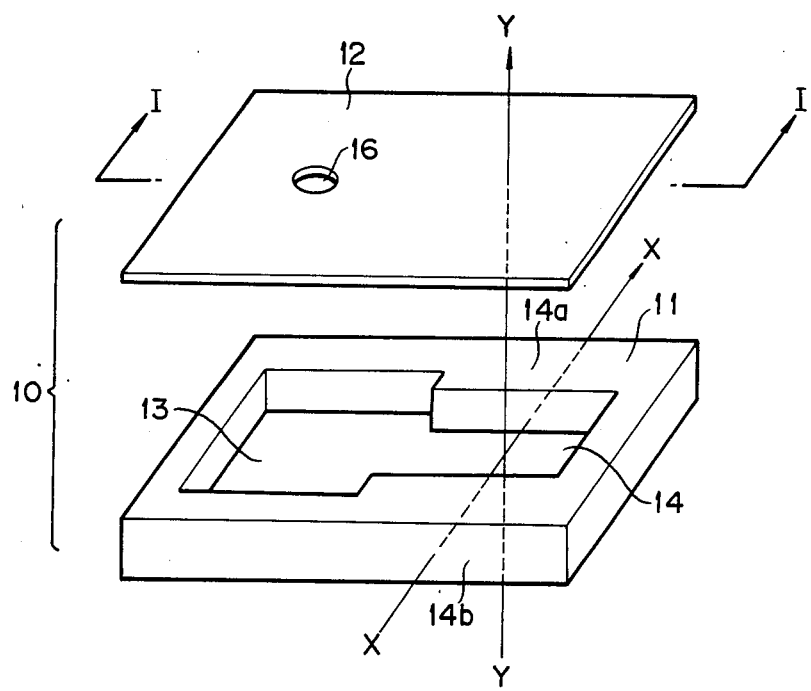
FIG. 2-B
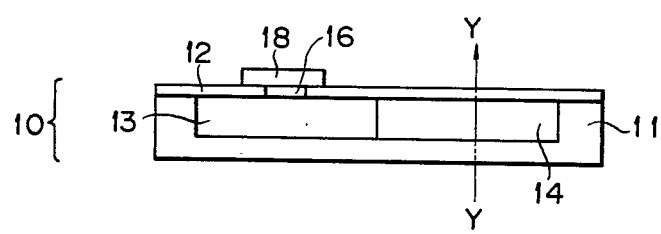

FLAT CONTAINER TYPE ANALYTICAL INSTRUMENT

BACKGROUND OF THE INVENTION

This is a continuation of application Ser. No. 676,054, filed Nov. 29, 1984 now abandoned.

1. Field of the Invention

The present invention relates to an integral flat container type analytical instrument for use in the analysis of an analyte present in a liquid sample and to a method for optical measurement of the analyte utilizing said analytical instrument.

2. Description of Prior Arts

There are known a wet process and a dry process as methods for quantitatively analyzing various components (hereinafter referred to as analyte) contained in liquid samples, particularly body fluids such as urine, saliva, blood and the like. The wet process has long been utilized and is carried out, for example, by reacting an analyte with a separately prepared reagent in a liquid phase in a container such as a test tube to effect a detectable change such as color formation and measuring such a change.

The wet process has an advantage of being capable of making the analysis with high accuracy, and at the same time it has disadvantages in that great skill in the analytical operation is required and anybody can not always conduct such an analytical operation quickly.

For this reason, attempts of performing the wet process with a simple container in a similar manner to that of the dry process have been made.

Japanese Patent Publication No. 46(1971)-25596 discloses an analytical pack which comprises a small envelope type container made of a flexible polymer material, an analytical reagent-storing zone located at one end of the container and a tube for introduction of a sample to be detected.

Japanese Patent Provisional Publication No. 57(1982)-156028 discloses a container type analytical instrument for use in the analysis of an analyte in a liquid sample, which is constructed, for example, in such a manner that the liquid sample is passed through a reaction zone where a reaction of the analyte with a reagent proceeds and a zone for detecting a detectable change produced by the reaction while controlling the liquid by means of a passage exhibiting a capillary action.

It can be said that these analytical instruments are useful. Nevertheless, in the former instrument, a reaction chamber composed of the small envelop-type container made of a flexible polymer material is employed at the same time as a chamber for detecting a detectable change such as color formation effected by the reactor (referred to herein as "observation chamber") so that the observation chamber is easily deformed. Accordingly, there is a disadvantage that the light path for measuring transmitted light in the observation chamber is hardly kept constant and a measuring equipment having a complicated structure is required for the analytical operation. Thus, the former analytical instrument has a problem in that quantitative analysis with high accuracy can not be conducted with a small, inexpensive measuring equipment having a simple structure. In the latter instrument, the passage between the reaction chamber and the observation chamber is one exhibiting a capillary action and hence, the instrument is suitable for use in specific analytical operation, but unsuitable for use in analysis in which a liquid sample must be thoroughly mixed with a reagent to expedite a rapid reaction therebetween.

The dry process is carried out by introducing a liquid sample into a sheet-form analytical element (often called analytical film) containing a reagent and optically detecting a change in color produced within said analytical element to analyze an analyte. The dry process has advantages in that the analytical operation is easy and the automating of the analysis with a smallsized measuring equipment is possible. Nevertheless, it has disadvantages in the satisfactory analytical accuracy is hardly accomplished in certain analytical system. Particularly, the dry process has a problem in that the process is unsuitable for use in the analysis of a turbid liquid formed by an analyte in a liquid sample, for example, in $ZnSO_4$ turbidity test (ZTT) and thymol turbidity test (TTT).

SUMMARY OF THE INVENTION

The present invention relates to a container type analytical instrument for analyzing analytes contained in liquid samples, particularly body fluids.

An object of the present invention is to provide an integral flat container type analytical instrument which is constructed of a simple structure, enables analysis to be easily carried out with a simple operation by anybody and is suitable for use in analyzing various analytes with common constructional instrument.

The present invention provides an integral flat container type analytical instrument for use in the quantitative analysis of an analyte present in a liquid sample which has a reaction chamber and an observation chamber associated with each other so as to allow a liquid to flow therebetween characterized in that:

(I) at least part of the wall of said reaction chamber is made of a flexible material;

(II) said observation chamber is provided with wall parts which are made of a transparent material and opposed to each other in such a manner that their relative positions are fixed to provide a given light path; and (III) no partition wall preventing the free flow of the liquid substantially exists between said reaction chamber and said observation chamber.

BRIEF DESCRIPTION OF THE DRAWINGS

FIG. 1-A is a perspective view showing an embodiment of the flat container type analytical instrument according to the present invention, and FIG. 1-B is a longitudinal sectional view taken along the line I—I in FIG. 1-A. In FIG. 1-A, the analytical instrument is shown in a state where the upper sheet-form wall part (lid) is detached.

FIG. 2-A is a perspective view showing another embodiment of the flat container type analytical instrument according to the present invention, and FIG. 2-B is a longitudinal sectional view taken along the line I—I in FIG. 2-A. In FIG. 2-A, the analytical instrument is shown in a state where the upper sheet-form wall part (lid) is detached.

DETAILED DESCRIPTION OF THE INVENTION

Figure 3:
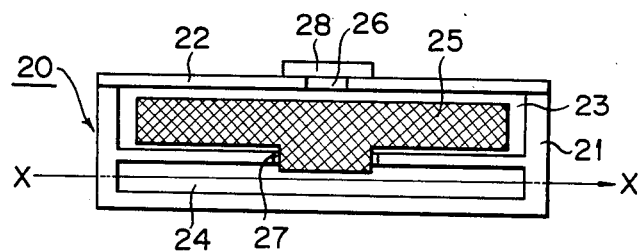
FIGS. 3 and 4 are sectional views showing the flat container type analytical instrument in other arrangements according to the present invention, respectively.

The flat container type analytical instrument of the present invention will be illustrated in more detail with reference to the accompanying drawings.

FIG. 1-A is a perspective view showing an embodiment of the flat container type analytical instruction of the present invention. FIG. 1-B illustrates a cross-sectional view of the analytical instrument taken along the line I—I in FIG. 1-A. In FIG. 1-A, the analytical instrument is shown in a state where the upper sheetform wall (lid) is detached.

Referring to FIGS. 1-A and 1-B, the analytical instrument 10 is composed of a plate-form container part 11 and an upper sheet-form wall part 12 and is in the form of a flat container as a whole, said container part 12 being made of a glass plate or a rigid or relatively antideformable synthetic resin material such as polyethylene, polypropylene, polystyrene, polymethacrylate ester resin, polyacrylate ester resin, bisphenol A polycarbonate, polyvinyl chloride or the like. Within the container part 11, there are arranged a reaction chamber 13 and an observation chamber 14 associated with each other in communicating relation so as to allow the liquid to flow therebetween. Within the reaction chamber 13, there is placed a porous material 15 having elasticity. As the porous material, there can be used a porous structure made from a resin material such as polyamide, cellulose acetate resin, polyvinyl chloride, polyethylene, polypropylene or polyurethane. Further, woven fabric, nonwoven fabric, felt, paper or a raw material thereof can be also used alone or in the form of a composite material with the above-mentioned porous resin. Preferably, the porous material should be in the form of a sheet from the viewpoint of deformation function which will be described hereinafter.

While FIG. 1-A shows the instrument in a state where an upper sheet-form wall part 12 is detached, the wall part 12 is water-tightly placed on the container part 11 to form the internal flat container type analytical instrument 10 as shown in FIG. 1-B.

The upper sheet-form wall part 12 is in the form of a relatively thin sheet composed of a flexible material (an elastomer or a composite material of an elastomer and a metallic sheet being particularly preferred), which shows flexibility when shaped into a thin sheet, for instance, a synthetic resin such as polyethylene terephthalate, polyamide or the like; an elastomer; a metallic material such as aluminum, copper, stainless steel or the like; or other flexible material. Thus, the wall part 12 can be easily deformed with a stress is applied thereto from the outside. Therefore, when a stress is intermittently applied to the upper sheet-form wall part 12 of the reaction chamber, restorable deformation is repeatedly produced in cooperation of the flexible sheet-form wall part 12 with the porous material 15. Such repeated restorable deformation produced in cooperation of the flexible sheet-form wall part 12 with the porous material 15 enables the thoroughly mixing of the reagent with the liquid sample introduced into the reaction chamber to be conducted so that an analyte present in the liquid sample can be rapidly brought into contact with the reagent. While an embodiment wherein the upper sheet-form wall part 12 is composed of a flexible material has been described above, the wall part 12 may be composed of a rigid material which hardly causes physical deformation or the wall part 12 may be a thick wall part and the bottom of the container part 11 may be composed of a flexible material instead. Alternatively, both the upper sheet-form wall part 12 and the bottom of the container part 11 may be composed of a flexible material.

Generally, the liquid sample is introduced into the reaction chamber 13 through a sample introducing port 16 provided in the upper sheet-form wall part 12. As the liquid sample, blood (whole blood, plasma or serum) as such can be used, or a diluted liquid sample may be used. Methods for diluting the liquid sample include a method wherein the liquid sample is previously diluted with a diluent and a method wherein the liquid sample and the diluent are separately introduced into the reaction chamber (either may be first introduced). The reagent which reacts with an analyte contained in the liquid sample and directly or indirectly produces a detectable change such as color formation, is previously charged in the reaction chamber 13, or is introduced through the sample introducing port 16 into the reaction chamber 13 at the time of carrying out the analysis. In order to rapidly and suitably perform the reaction between the analyte and the reagent in the reaction chamber 13, it is desirable to store the reagent, for example, by impregnating the porous material with the reagent or by coating the reagent on the inner wall of the reaction chamber. The reagent may be in a dry form (solid) in a semidry form (jelly) or in a liquid form. The solid reagent may be in the form of granule or powder. Usually, the sample introducing port 16 is closed by means of a lid 18 for the sample introducing port after the sample is introduced into the reaction chamber 13.

The observation chamber 14 provides a zone where a sample solution showing a detectable change such as color formation generated by the contact of the analyte with the reagent in the reaction chamber 13 is received and the change is detected by mainly a optical means to analyze the analyte. The observation chamber 14 is provided with wall parts 14a and 14b made of a transparent material and opposed to each other in such a manner that their relative positions are fixed to provide a given light path. The space between the transparent wall parts 14a and 14b is kept constant so as to provide a fixed light path so that when the absorption, the scattering and the reflection, in the direction of the line X—X, of light passing therethrough are photometrically detected, the change of the sample solution received in the observation chamber 14 can be easily measured with high accuracy. Thus, the optical measurement of the liquid introduced into the observation chamber from the reaction chamber after completion of a reaction can be performed along a light path in parallel with the bottom face of the instrument.

While the light path in the observation chamber 14 has been set in the direction (X—X direction) parallel to the plane of the flat analytical instrument 10 in the above embodiment, this light path can be set in other direction, for example, in the direction (Y—Y direction) perpendicular to the plane of the instrument 10 shown in FIGS. 1-A and 1-B. In this case, however, it is necessary that the bottom and the upper wall part 12 of the observation chamber 14 are composed of a rigid material so that they are not affected by the deformation of the reaction chamber.

No partition wall which substantially prevents the flow of the liquid exists between the reaction chamber 13 and the observation chamber 14. This means that between the reaction chamber 13 and the observation chamber 14 there is provided no partition wall function (for example, capillary action, dialysis action due to semipermeable membrane, etc.) which can not be externally controlled by artificial pressure (for example, pressing against the reaction chamber by the hand of an analyst). Thus, when the mixing of the reagent with the liquid sample introduced into the reaction chamber is conducted, the observation chamber functions as part of the reaction chamber so that the mixing can be carried out easily and sufficiently. Further, after the analyte is brought into contact with the reagent, the resulting sample solution can be quickly transferred to the observation chamber so that analytical operation can be easily accelerated. However, it is possible to provide, for example, a net interfering with the transfer of solids or a filtering sheet, provided that they do not interfere with the free flow of the liquid between the reaction chamber and the observation chamber. It is preferred to provide an air vent means such as pin holes having a pore size capable of ignoring the leakage of the liquid in the observation chamber at a position apart from the side of the reaction chamber.

While FIGS. 1-A and 1-B show an embodiment of the flat container type analytical instrument of the present invention wherein a porous material having elasticity is provided within the reaction chamber, the provision of the porous material can be omitted, as seen in FIGS. 2-A and 2-B. In FIGS. 2-A and 2-B, the numerals stand for the same meaning respectively as given in FIGS. 1-A and 1-B.

Moreover, while FIGS. 1-A and 1-B show an embodiment of the flat container type analytical instrument of the present invention wherein the reaction chamber and the observation chamber are on the same plane with each other, the positional relationship therebetween is not limited thereto and the reaction chamber and the observation chamber can be arranged in a laminated from.

FIG. 3 is a longitudinal sectional view showing a flat container type analytical instrument 20 according to the present invention wherein a reaction chamber 24 and an observation chamber 25 are arranged in a laminated form.

The analytical instrument 20 comprises a planar container part 21 and an upper sheet-form wall part 22 composed of a flexible wall part 22, and is in the form of a flat container as a whole as in FIGS. 1-A and 1-B. Within the container part 21, there are arranged the reaction chamber 23 and the observation chamber 24 associated with each other in communicating relation through an opening part so as to allow the liquid to freely flow there between. Within the reaction chamber 23, there can be placed a porous material 25 having elasticity. Preferably, the porous material is in a form having a convex part extending through the opening part to the observation chamber (to such an extent that the convex part does not interfere with a light path for measurement in the observation chamber). The mixing of the liquid sample with the reagent is conducted in the presence of said convex part so that when pressure is intermittently applied to the wall of the reaction chamber, the liquid run into the observation chamber is positively restored to the reaction chamber and the mixing is thoroughly done. When the analytical instrument is turned upside down and the mixing is conducted in the inverted state, the convex part is not always necessary.

In the analytical instruments in other forms, the porous material can be also provided with such a convex part extending to the observation chamber.

The analytical operation using the instrument in the laminated form as shown in FIG. 3 can be carried out in a similar manner to that described above. A liquid sample is is introduced through a sample introducing port 26, the port 26 is then closed by means of a lid 28 for the sample introducing port and a pressure is intermittently applied to the flexible upper sheet-form wall part 22 of the reaction chamber 23 from the outside to cause repeatedly restorable deformation in cooperation with the elastic porous material 25, whereby the liquid sample is thoroughly mixed with the reagent to effect the reaction between an analyte and the reagent. The resulting sample solution is then transferred to the observation chamber to perform an optical measurement.

Figure 4:
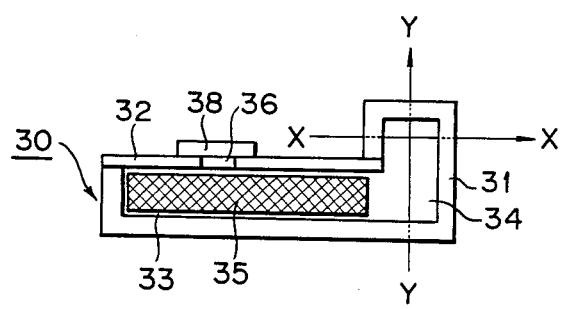

FIG. 4 is a longitudinal sectional view showing a flat container type analytical instrument 30 according to the present invention wherein a reaction chamber 33 and an observation chamber 34 are provided in other arrangement.

The analytical instrument 30 comprises a planar container part 31 and an upper sheet-form wall part 32 composed of a flexible material and is in a flat plate form as a whole. Within the container part 31, there are provided the reaction chamber 33 and the observation chamber 34 associated with each other in communicating relation in a horizontal direction and so arranged as to allow the liquid to freely flow therebetween. In this embodiment, the observation chamber 34 is in a vertically extended form. Within the reaction chamber 33, there can be placed a porous material 35 having elasticity.

The analytical operation using the instrument of FIG. 4 can be conducted in a similar manner to that described above. The liquid sample is introduced through a sample introducing port 36, the port 36 is then closed by means of a lid 38 for the sample introducing port and a pressure is intermittently applied to the flexible upper sheet-form wall part 32 of the reaction chamber 33 from the outside to cause repeatedly restorable deformation in cooperation with the elastic porous material 35, whereby the liquid sample is thoroughly mixed with the reagent to effect the reaction between an analyte and the reagent. The resulting sample solution is then transferred to the observation chamber 34 to make an optical measurement.

The light path for the optical measurement can be set in various directions in the analytical instrument 30 of FIG. 3. For example, the light path can be set in the direction parallel or approximately parallel to the base of the analytical instrument 30 (for example, in the direction of the line X—X in FIG. 3, or in the direction parallel to the base and perpendicular to the line X—X), or in the direction perpendicular or approximately perpendicular to the base of the analytical instrument 30 (for example, in the direction of the line Y—Y in FIG. 4).

There are no limitations with regard to samples and analytes to be analyzed using the flat analytical instrument of the present invention. Any of various samples and analytes which have been conventionally subjected to analytical operations in the wet process and the dry process can be subjected to the analytical operation using the analytical instrument of the present invention. In other words, the analytical instrument of the present invention can be widely applied, in a common basic structure, to biochemical analysis, immunological analysis, hematological analysis, medicinal analysis, general test and analysis, etc.

Example of such analyses include:

(1) a system for colorimetrically measuring glucose content in serum in such a manner that the elastic porous material is impregnated with reagents, such as glucose oxidase, peroxidase, 4-aminoantipyrine and 1,7-dihydroxynaphthalene, and placed in the reaction chamber to provide a flat contaiiner type analytical instrument for measuring glucose content in blood; serum as a liquid sample is introduced through the sample introducing port into the reaction chamber, deionized distilled water as a diluent is then introduced into the reaction chamber, the reagent, serum and distilled water are thoroughly mixed together, the resulting colored reaction solution is transferred to the observation chamber by pushing the upper wall part and transmission optical density at a light pass length is measured using visible rays with a central wavelength at 505 nm to measure colorimetrically glucose content in serum;

(2) a system for colorimetrically measuring the activity value of glutamic-oxaloacetic transaminase (aspartate aminotransferase) in serum in such a manner that L-aspartic acid, -ketoglutaric acid, NADH (nicotinamide adenine dinucleotide reduction type), lactic dehydrogenase, malic dehydrogenase and a buffer solution (pH 7.4) are incorporated in the porous material which is then placed in the reaction chamber; serum as a liquid solution and deionized distilled water as a diluent are introduced into the reaction chamber, and transmission optical density at a light pass length is measured using near ultraviolet rays with a central wavelength at 340 nm to colorimetrically measure the active value of glutamicoxaloacetic transaminase (aspartate aminotransferase) in serum;

(3) a system for colorimetrically determining ZTT value in serum in such a manner that barbital and barbital sodium are incorporated in the porous material which is then washed with an aqueous zinc sulfate solution and placed in the reaction chamber; serum (liquid sample) is introduced into the reaction chamber and thoroughly stirred, the resulting sample solution is transferred to the observation chamber, and transmission optical density at a light pass length is measured using visible rays with a central wavelength at 660 nm to determine colorimetrically ZTT value in serum; and (4) a system for colorimetrically determining $\beta$-lipoprotein content in serum in such manner that anti-$\beta$-lipoprotein antibody is incorporated in the porous material which is then placed in the reaction chamber, a liquid sample (serum) containing $\beta$-lipoprotein is introduced into the reaction chamber and thoroughly mixed to allow an immunological reaction to proceed, the resulting turbid solution is transferred to the observation chamber, and transmission optical density in respect of turbidity at a light path length is measured using a light with a central wavelength at 550 nm to measure colorimetrically $\beta$-lipoprotein content in serum.

We claim:

1. An integral flat analytical element for use in the quantitative analysis of an analyte present in a liquid sample which comprises a flat container having a lid and a bottom, the lid having a sample introduction port therein, the lid, the bottom, or both being flexible and restorably deformable, said container comprising a reaction chamber and an observation chamber in liquid communication with each other, the reaction chamber containing a porous material which is elastomerically deformable positioned between the lid and bottom such that deformation of the lid, bottom, or both, causes deformation of the porous material, said observation chamber having at least two rigid transparent side wall portions opposed to each other in fixed positions to provide a predetermined light path.

2. The analytical instrument as claimed in claim 1, wherein a reagent is contained in said reaction chamber.

3. The analytical instrument as claimed in claim 1, wherein said reaction chamber and said observation chamber are positioned substantially on the same plane.

4. The analytical instrument as claimed in claim 1, wherein said reaction chamber and said observation chamber are superposed one on another.

5. A method for the optical measurement of an analyte in a liquid sample utilizing an integral flat analytical element which comprises a flat container having a lid and a bottom, the lid having a sample introduction port therein, the lid, the bottom, or both being flexible and restorably deformable, said container comprising a reaction chamber, and an observation chamber in liquid communication with each other, the reaction chamber containing a reagent which is reactive with the analyte, said observation chamber having at least two rigid transparent side wall portions opposed to each other in fixed positions to provide a predetermined light path, said reaction chamber containing a reagent which is reactive with said analyte; and introducing a liquid sample into the reaction chamber through the sample introduction port;

repeatedly applying stress to the flexible bottom, lid, or both of the instrument to mix the liquid sample with the reagent and cause a reaction between the analyte in the liquid sample and the reagent in the reaction chamber; and photometrically observing a detectable change produced in the liquid by the reaction of the analyte and the reagent utilizing the transparent side wall portions of the observation chamber.

6. The method of claim 5 wherein the reaction chamber contains a porous material which is elastomerically deformable positioned between the lid and bottom such that deformation of the lid, bottom, or both, causes deformation of the porous material, and the reagent is contained in the porous material.

7. The method as claimed in claim 5, wherein said reaction chamber and said observation chamber are positioned substantially on the same plane.

8. The method as claimed in claim 5, wherein said reaction chamber and said observation chamber are superposed one on another.

* * * * *